United States Patent
Miller et al.

(10) Patent No.: US 7,763,764 B2
(45) Date of Patent: Jul. 27, 2010

(54) HYDROCARBON CONVERSION PROCESSES USING THE UZM-27 FAMILY OF CRYSTALLINE ALUMINOSILICATE COMPOSITIONS

(75) Inventors: Mark A. Miller, Niles, IL (US); Gregory J. Lewis, Santa Cruz, CA (US)

(73) Assignee: UOP LLC, Des Plaines, IL (US)

( * ) Notice: Subject to any disclaimer, the term of this patent is extended or adjusted under 35 U.S.C. 154(b) by 60 days.

(21) Appl. No.: 12/337,723

(22) Filed: Dec. 18, 2008

(65) Prior Publication Data
US 2010/0160701 A1    Jun. 24, 2010

(51) Int. Cl.
*C07C 5/66* (2006.01)
*C07C 2/12* (2006.01)
*C07C 5/27* (2006.01)
*C10G 73/02* (2006.01)

(52) U.S. Cl. .................. 585/467; 585/418; 585/533; 208/27

(58) Field of Classification Search ........... 585/467, 585/418, 533; 208/27
See application file for complete search history.

(56) References Cited

U.S. PATENT DOCUMENTS

| 4,310,440 A | 1/1982 | Wilson et al. ............ 252/435 |
| 4,440,871 A | 4/1984 | Lok et al. ............... 502/214 |
| 5,157,196 A | 10/1992 | Crossland et al. ......... 585/720 |
| 5,157,197 A | 10/1992 | Cooper et al. ............ 585/726 |
| 6,776,975 B2 | 8/2004 | Wilson et al. ............ 423/713 |
| 2005/0095195 A1 | 5/2005 | Lewis et al. ............. 423/705 |

OTHER PUBLICATIONS

U.S. Appl. No. 12/337,719, filed Dec. 18, 2008, Mark A. Miller et al.

*Primary Examiner*—Thuan Dinh Dang
(74) *Attorney, Agent, or Firm*—Frank S Molinaro

(57) ABSTRACT

This invention relates to hydrocarbon conversion processes using a new family of crystalline aluminosilicate compositions designated the UZM-27 family. These include the UZM-27 and UZM-27HS which have unique structures. UZM-27 is a microporous composition which has a three-dimensional structure and is obtained by calcining the as synthesized form designated UZM-27P. UZM-27HS is a high silica version of UZM-27 and includes an essentially pure silica version of UZM-27.

2 Claims, No Drawings

HYDROCARBON CONVERSION PROCESSES USING THE UZM-27 FAMILY OF CRYSTALLINE ALUMINOSILICATE COMPOSITIONS

FIELD OF THE INVENTION

This invention relates to hydrocarbon conversion processes using a new family of crystalline aluminosilicate compositions designated the UZM-27 family. These include the UZM-27 and UZM-27HS which have unique structures. UZM-27 is a microporous composition which has a three-dimensional structure and is obtained by calcining the as synthesized form designated UZM-27P. UZM-27HS is a high silica version of UZM-27 and includes an essentially pure silica version of UZM-27.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

Applicants have successfully prepared a new family of crystalline aluminosilicate compositions designated UZM-27. The family includes an as-synthesized layered composition designated UZM-27P and a calcined three dimensional microporous zeolitic composition designated UZM-27. The topologies of these UZM-27 family members are distinct from each other and other aluminosilicate species in the prior art. The layered composition can also be expanded and exfoliated by using cationic surfactants. The as-synthesized layered composition, UZM-27P, is prepared using a structure directing agent such as trimethylbutylammonium hydroxide, $[CH_3(CH_2)_3NMe_3]^+OH^-$, plus an alkali earth metal such as $Ca^{2+}$ using the Charge Density Mismatch Process for synthesizing zeolites as described in US Patent Application Publication No. 2005/0095195.

SUMMARY OF THE INVENTION

As stated, the present invention relates to hydrocarbon conversion processes using a new family of crystalline compositions designated UZM-27.

Accordingly, one embodiment of the invention is a hydrocarbon conversion process comprising contacting a hydrocarbon stream with a crystalline microporous zeolitic composition at hydrocarbon conversion conditions to give a converted product, the crystalline zeolitic microporous composition having a three-dimensional framework composed of at least tetrahedral $SiO_2$ units designated UZM-27. UZM-27 has an empirical composition on an anhydrous basis expressed by the empirical formula of:

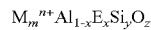

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 10 to about 35 and "z" is the mole ratio of O to (Al+E) and has a value determined by the equation:

$$z = (m \cdot n + 3 + 4 \cdot y)/2$$

and is characterized in that it has an x-ray diffraction pattern having at least the d-spacings and intensities set forth in Table B:

TABLE B

| 2Θ | d(Å) | $I/I_0$ % | peaks |
|---|---|---|---|
| 4.03-4.57 | 21.91-19.32 | m-vs | |
| 9.40-10.20 | 9.40-8.67 | m | |
| 10.25-10.80 | 8.62-8.19 | m | |
| 12.65-13.45 | 6.99-6.58 | s-vs | |
| 19.55-19.87 | 4.54-4.46 | m-s | br |
| 21.32-21.72 | 4.16-4.09 | m | br |
| 24.25-24.75 | 3.67-3.59 | m-s | sh |
| 25.65-26.48 | 3.47-3.36 | vs | br |
| 29.75-31.01 | 3.00-2.88 | m | br |
| 49.72-50.13 | 1.83-1.82 | m | |

These and other objects and embodiments of the invention will become more apparent after the detailed description of the invention.

DETAILED DESCRIPTION OF THE INVENTION

Applicants have prepared a series of crystalline compositions designated the UZM-27 family of compositions which include the as synthesized composition, UZM-27P and a calcined composition, UZM-27 and which have uses in various hydrocarbon conversion processes. Each of these species has a unique topology/structure. While UZM-27P is a layered composition, the calcined product, UZM-27 is a microporous three dimensional zeolitic composition. UZM-27P has an empirical composition in the as-synthesized form and on an anhydrous basis expressed by the empirical formula:

where M is at least one exchangeable cation and is selected from the group consisting of alkali metal ions, alkaline earth metal ions, and rare earth metal ions. Specific examples of the M cations include but are not limited to lithium, sodium, potassium, rubidium, cesium, calcium, strontium, barium, lanthanum, ytterbium and mixtures thereof, with calcium being preferred. R is an organoammonium cation or an amine, examples of which include but are not limited to the trimethylbutylammonium cation, diquat-4, choline cation $[(CH_3)_3NCH_2CH_2OH]^+$, ethyltrimethylammonium, diethyldimethylammonium, ethyltrimethylpropylammonium, trimethylpentylammonium, dimethyldiethanolammonium, tetraethylammonium ($TEA^+$), tetrapropylammonium $TPA^+$, dimethylbutylamine, diethanolamine and mixtures thereof and "r" is the mole ratio of R to (Al+E) and varies from about 0.5 to about 10.0. Trimethylbutylammonium is a preferred organoammonium cation. The value of "p" which is the weighted average valence of R varies from 1 to about 2. The value of "n" which is the weighted average valence of M varies from about 1 to about 3 while "m" is the mole ratio of M to (Al+E) and varies from 0.05 to about 10. The ratio of silicon to (Al+E) is represented by "y" which varies from about 10 to about 35. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z = (m \cdot n + p \cdot r + 3 + 4 \cdot y)/2.$$

When M is only one metal, then the weighted average valence is the valence of that one metal, i.e. +1 or +2.

However, when more than one M metal is present, the total amount of:

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

When more than one organoammonium cation is present, the total amount of $$R_r^{p+} = R_{r1}^{(p1)+} + R_{r2}^{(p2)+} + R_{r3}^{(p3)+} + \ldots$$

And the weighted average valence "p" is given by the equation:

$$p = \frac{r_1 \cdot p_1 + r_2 \cdot p_2 + r_3 \cdot p_3 + \ldots}{r_1 + r_2 + r_3 \ldots}$$

UZM-27P is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals include the halide salts, nitrate salts, acetate salts, and hydroxides of the respective alkali, alkaline earth, or rare earth metals. R is an organoammonium cation or an amine selected from the group consisting of trimethylbutylammonium, diquat-4, pentyltrimethylammonium, choline, ethyltrimethylammonium, diethyldimethylammonium, TEA, TPA, trimethylpropylammonium, dimethyldiethanolammonium, dimethylbutylamine, diethanolamine and mixtures thereof, and the sources include the hydroxide, chloride, bromide, iodide and fluoride compounds. Specific examples include without limitation trimethylbutylammonium hydroxide and trimethylbutylammonium chloride, pentyltrimethylammonium hydroxide, ethyltrimethylammonium hydroxide, diethyldimethylammonium hydroxide, tetraethylammonium hydroxide, tetrapropylammonium hydroxide, tetrapropylammonium chloride.

The reaction mixture containing reactive sources of the desired components can be described in terms of molar ratios of the oxides by the formula:

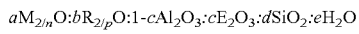

$$a\text{M}_{2/n}\text{O}:b\text{R}_{2/p}\text{O}:1\text{-}c\text{Al}_2\text{O}_3:c\text{E}_2\text{O}_3:d\text{SiO}_2:e\text{H}_2\text{O}$$

where "a" varies from about 0.05 to about 10.0, "b" varies from about 2.5 to about 120, "c" varies from 0 to 1.0, "d" varies from about 20 to about 120, and "e" varies from about 50 to about 6000. If alkoxides are used, it is preferred to include a distillation or evaporative step to remove the alcohol hydrolysis products. The reaction mixture is now reacted at a temperature of about 100° C. to about 200° C. and preferably from about 125° C. to about 175° C. for a period of about 1 day to about 3 weeks and preferably for a time of about 3 days to about 10 days in a sealed reaction vessel under autogenous pressure. After crystallization is complete, the solid product is isolated from the reaction mixture by means such as filtration or centrifugation, and then washed with deionized water and dried in air at ambient temperature up to about 100° C. A preferred synthetic approach to make UZM-27P utilizes the charge density mismatch process disclosed in US Patent Application Publication No. US 2005/0095195 which is incorporated by reference in its entirety. The charge density mismatch process allows multiple structure directing agents to cooperate to crystallize a single structure. The method employs appropriate quaternary ammonium hydroxides to solubilize aluminosilicate species, creating a reaction mixture which has difficulty crystallizing and condensing to form a solid under synthesis conditions. These preformed aluminosilicate species require crystallization-inducing agents such as alkali and alkaline earth metals and more highly charged organoammonium cations that are separately introduced and cooperate with the quaternary ammonium template to affect the crystallization process. A preferred combination for the synthesis of UZM-27P is trimethylbutylammonium hydroxide as the charge density mismatch template and calcium as the crystallization inducing agent.

The UZM-27P crystalline layered aluminosilicate, which is obtained from the above-described process, is characterized by an x-ray diffraction pattern having at least the d-spacings and relative intensities set forth in Table A below.

TABLE A

| 2Θ | d(Å) | $I/I_0$ % | peaks |
|---|---|---|---|
| 3.98-4.14 | 22.18-21.33 | m-vs | |
| 7.90-8.68 | 11.18-10.18 | m-vs | |
| 10.55-10.84 | 8.38-8.16 | w-m | |
| 12.72-13.16 | 6.95-6.72 | m | |
| 17.00-17.12 | 5.21-5.18 | m | |
| 20.70-21.50 | 4.29-4.13 | m | br |
| 24.44-24.61 | 3.64-3.61 | m-s | sh |
| 25.57-26.00 | 3.48-3.42 | vs | br |
| 28.84-29.45 | 3.09-3.03 | w-m | br |
| 49.92-50.19 | 1.83-1.82 | m-s | |

UZM-27P is a layered composition and can be converted to a microporous crystalline three-dimensional aluminosilicate zeolite, UZM-27, by calcination. The condensation of the layers to form the microporous three-dimensional UZM-27 occurs at calcination temperatures greater than 400° C. and preferably at temperatures greater than 500° C. for times sufficient to decompose and remove the organoammonium template and effect condensation. The time can vary considerably but is usually from about 3 hr to about 24 hr. The resulting UZM-27 is characterized by a three-dimensional framework composed of at least tetrahedral SiO$_2$ units and an empirical composition on an anhydrous basis expressed by the empirical formula of:

$$M_m^{n+}Al_{1-x}E_xSi_yO_z$$

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 10 to about 35 and "z" is the mole ratio of O to (Al+E) and has a value determined by the equation:

$$z = (m \cdot n + 3 + 4 \cdot y)/2$$

Where M is only one metal, then the weighted average valence is the valence of that one metal, i.e. +1 or +2.

However, when more than one M metal is present, the total amount of:

$$M_m^{n+} = M_{m1}^{(n1)+} + M_{m2}^{(n2)+} + M_{m3}^{(n3)+} + \ldots$$

and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

and is characterized in that it has the x-ray diffraction pattern having at least the d-spacings and intensities set forth in Table B:

TABLE B

| 2Θ | d(Å) | I/I$_0$ % | peaks |
|---|---|---|---|
| 4.03-4.57 | 21.91-19.32 | m-vs | |
| 9.40-10.20 | 9.40-8.67 | m | |
| 10.25-10.80 | 8.62-8.19 | m | |
| 12.65-13.45 | 6.99-6.58 | s-vs | |
| 19.55-19.87 | 4.54-4.46 | m-s | br |
| 21.32-21.72 | 4.16-4.09 | m | br |
| 24.25-24.75 | 3.67-3.59 | m-s | sh |
| 25.65-26.48 | 3.47-3.36 | vs | br |
| 29.75-31.01 | 3.00-2.88 | m | br |
| 49.72-50.13 | 1.83-1.82 | m. | |

Another embodiment of the UZM-27 family of crystalline compositions is derived from the ion-exchange of UZM-27P with an organoammonium cation different from the starting organoammonium cation. As such, the layers may be "expanded" or exfoliated with appropriate organoammonium salts such as cetyltrimethylammonium. These compositions are highly variable with respect to an x-ray diffraction pattern. Such expanded compositions may also be further exchanged with pillaring agents, such as [Al$_{13}$O$_4$(OH)$_{24}$(H$_2$O)$_{12}$]$^{7+}$ or [Zr$_4$(OH)$_8$(H$_2$O)$_{16}$]$^{8+}$ followed by calcination to make new microporous compositions.

The microporous UZM-27 composition will contain some of the exchangeable or charge balancing cations in its pores. These exchangeable cations can be exchanged for other cations. The UZM-27 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4 in U.S. Pat. No. 6,776,975 B1 which is incorporated by reference in its entirety. Properties that can be modified include porosity, adsorption, Si/Al ratio, acidity, thermal stability, etc.

The UZM-27 composition which is modified by one or more techniques described in the '975 patent (herein UZM-27HS) is described by the empirical formula on an anhydrous basis of:

$$M1'^{n+}_aAl_{(1-x)}E_xSi_{y'}O_{z'}$$

where M1' is at least one exchangeable cation selected from the group consisting of alkali, alkaline earth metals, transitions metals, rare earth metals, ammonium ion, hydrogen ion and mixtures thereof, "a" is the mole ratio of M1' to (Al+E) and varies from about 0.01 to about 50, "n" is the weighted average valence of M1' and has a value of about +1 to about +3, E is an element selected from the group consisting of gallium, iron, boron, and mixtures thereof, "x" is the mole fraction of E and varies from 0 to 1.0, y' is the mole ratio of Si to (Al+E) and varies from greater than 15 to virtually pure silica and z' is the mole ratio of O to (Al+E) and has a value determined by the equation:

$$z' = (a \cdot n + 3 + 4y')/2$$

By virtually pure silica is meant that virtually all the aluminum and/or the E metals have been removed from the framework. It is well know that it is virtually impossible to remove all the aluminum and/or E metal. Numerically, a zeolite is virtually pure silica when y' has a value of at least 3,000, preferably 10,000 and most preferably 20,000. Thus, ranges for y' are from 15 to 3,000 preferably greater than 30 to about 3,000; 15 to 10,000 preferably greater than 30 to about 10,000 and 15 to 20,000 preferably greater than 30 to about 20,000.

In specifying the proportions of the zeolite starting composition or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-27 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-27 zeolite of this invention can also be used as a catalyst or catalyst support in various hydrocarbon conversion processes. Hydrocarbon conversion processes are well known in the art and include cracking, hydrocracking, alkylation of both aromatics and isoparaffin, isomerization, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871, which are incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of 400° to 1200° F. (204-649° C.), preferably between 600° and 950° F. (316-510° C.). Reaction pressures are in the range of atmospheric to about 3,500 psig (24,132 kPa g), preferably between 200 and 3000 psig (1379-20,685 kPa g). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 1,000 to 50,000 standard cubic feet (scf) per barrel of charge (178-8,888 std. $m^3/m^3$), preferably between 2,000 and 30,000 scf per barrel of charge (355-5,333 std. $m^3/m^3$). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the UZM-27 composition using feedstocks such as gas oils, heavy naphthas, deasphalted crude oil residua, etc. with gasoline being the principal desired product. Temperature conditions of 850° to 1100° F., LHSV values of 0.5 to 10 and pressure conditions of from about 0 to 50 psig are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 5:1 and 30:1, a LHSV of about 0.3 to about 6 $hr^{-1}$, a temperature of about 100° to about 250° C. and pressures of about 200 to about 1000 psig. Further details on apparatus may be found in U.S. Pat. No. 4,870,222 which is incorporated by reference.

Alkylation of isoparaffins with olefins to produce alkylates suitable as motor fuel components is carried out at temperatures of –30° to 40° C., pressures from about atmospheric to about 6,894 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structures of the UZM-27 family of aluminosilicate compositions of this invention were determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 70° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline compositions from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

w=0-15; m=15-60; s=60-80 and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present. Finally, some peaks are identified with special identifiers as follows: very broad(vbr); broad (br); and shoulder (sh).

In order to more fully illustrate the invention, the following examples are set forth. It is to be understood that the examples are only by way of illustration and are not intended as an undue limitation on the broad scope of the invention as set forth in the appended claims.

EXAMPLE 1

Trimethylbutylammonium Hydroxide (TMBAOH) Solution

A typical TMBAOH solution was prepared as follows. Trimethylbutylammonium iodide, 1466.3 g, was dissolved in 1948.6 g deionized water in a 5 liter 3-necked round bottom flask equipped with overhead stirring. A 1 wt. % excess of silver(I) oxide, (99%), 712 g, was added and stirred in the dark for 24 hours. The resulting trimethylbutylammonium hydroxide solution was isolated by filtration.

Standardization of the trimethylbutylammonium hydroxide solution via titration with potassium acid phthalate to a phenolphthalein endpoint showed the solution to be 31.54 wt. % trimethylbutylammonium hydroxide.

EXAMPLE 2

Trimethylbutylammonium Aluminosilicate Solution

Trimethylbutylammonium hydroxide, (25.66%), 439.65 g, was diluted with 99.26 g de-ionized water while stirring. Aluminum tri sec-butoxide, (97%), 115.86 g, was added to the solution, which was then cooled in ice prior to the addition of tetraethylorthosilicate, (98%), 200.0 g with stirring. After hydrolysis was complete, the solution was transferred to a rotary evaporator to remove alcohol. A total of 163.7 g. of liquid was removed. Elemental analysis showed the solution to contain 4.36 wt. % Si and 2.04 wt. % Al.

EXAMPLE 3

Trimethylbutylammonium Silicate Solution

Trimethylbutylammonium hydroxide, (25.66%), 366.4 g, was diluted with 564.8 g deionized water and to it there were added 500.0 g of tetraethylorthosilicate, (98%) with stirring. After hydrolysis was complete, the solution was placed on a rotary evaporator to remove the alcohol. Elemental analysis showed the solution to contain 7.04 wt % Si.

EXAMPLE 4

A mixture was formed by adding to a beaker with stirring, 57.51 g of trimethylbutylammonium silicate solution (Example 3), 8.59 g of trimethylbutylammonium aluminosilicate solution (Example 2), and 40.68 g of trimethylbutylammonium hydroxide (31.54%, Example 1). To this mixture there was added dropwise (with stirring) 8.57 g of a calcium acetate solution $(Ca(OAc)_2*40\ H_2O)$. The resulting mixture was stirred for an additional hour and the reaction mixture was then divided equally among four 45 ml Teflon® lined autoclaves. The reaction mixtures were digested at 150° C. for 3, 7, 10, and 14 days respectively.

The solid product from each autoclave was recovered by filtration, washed with de-ionized water and dried at 95° C. The products obtained from all the reactions were identified to be UZM-27P by x-ray diffraction (XRD) analysis. Representative diffraction lines for the product isolated after 7 days are given below in Table 1. Elemental analysis showed the product to consist of elements with the following mole ratios: Si/Al=20.90, Ca/Al=1.24, N/Al=2.42, and C/N=4.20.

TABLE 1

| 2Θ | d(Å) | $I/I_0$ % | peaks |
|---|---|---|---|
| 4.02 | 21.96 | vs | |
| 8.18 | 10.80 | vs | |
| 10.62 | 8.32 | w | |
| 13.06 | 6.77 | m | |
| 17.06 | 5.19 | m | |
| 21.11 | 4.21 | m | br |
| 24.55 | 3.62 | s | sh |
| 25.88 | 3.44 | vs | br |
| 29.33 | 3.04 | w | br |
| 50.10 | 1.82 | s | |

EXAMPLE 5

An aluminosilicate reaction mixture was prepared by first dissolving 10.54 g of aluminum tri sec-butoxide (95+%) in 357.74 g of trimethylbutylammonium hydroxide, (31.54%, Example 1), with vigorous stirring, followed by the addition of 122.46 g de-ionized water. The resulting mixture was cooled in an ice bath before adding 200.0 g tetraethylorthosilicate, (98%). The reaction mixture was homogenized for 1 hour and then transferred to a rotary evaporator to remove alcohol. Elemental analysis showed the resulting solution to contain 5.28 wt. % Si and 0.22 wt. % Al.

A 150.0 g portion of the solution was placed in a container and to it there was added dropwise with stirring 14.06 g of a calcium acetate solution, $(Ca(OAc)_2*40\ H_2O)$. The resultant reaction mixture was homogenized for an additional hour and then divided equally among six 45 cc Teflon®-lined autoclaves and reacted at 175° C. for 3, 5, 7, 10, 14, and 21 days.

The solid product from each autoclave was recovered by filtration, washed with de-ionized water and dried at 95° C. The product obtained from the autoclaves digested for 3 and 5 days was identified to be UZM-27P by XRD analysis. Representative diffraction lines for the product from one of the autoclaves are shown in Table 2 below. Elemental analysis showed the product to consist of elements with the following mole ratios: Si/Al=21.21, Ca/Al=1.53, N/Al=2.66 and C/N=4.01.

TABLE 2

| 2Θ | d(Å) | $I/I_0$ % | peaks |
|---|---|---|---|
| 4.06 | 21.75 | vs | |
| 8.08 | 10.93 | s | |
| 10.70 | 8.27 | m | |
| 12.82 | 6.90 | m | |
| 17.08 | 5.19 | m | |
| 20.88 | 4.25 | m | br |
| 24.5 | 3.63 | s | sh |
| 25.68 | 3.47 | vs | br |
| 29.27 | 3.05 | m | br |
| 50.06 | 1.82 | m | |

EXAMPLE 6

The as-synthesized UZM-27P product from example 5 was exchanged with $NH_4NO_3$ by suspending 2 g of the UZM-27P powder in 500 g 0.5 M $NH_4NO_3$ solution at 75° C. for an hour with stirring. The exchanged product was isolated by filtration and washed with deionized water. The process was repeated two more times. The solid product was dried at 95° C. and identified to be UZM-27P by XRD analysis. Representative diffraction lines for the product are shown in Table 3 below. Elemental analysis showed the composition of the product to consist of the following mole ratios: Si/Al=18.75 and Ca/Al=0.82.

TABLE 3

| 2Θ | d(Å) | $I/I_0$ % | peaks |
|---|---|---|---|
| 4.10 | 21.55 | m | |
| 8.50 | 10.39 | s | |
| 10.77 | 8.21 | w | |
| 13.06 | 6.77 | m | |
| 17.06 | 5.19 | m | |
| 19.56 | 4.53 | m | br |
| 21.34 | 4.16 | m | br |
| 24.50 | 3.63 | m | sh |
| 25.90 | 3.44 | vs | br |
| 28.97 | 3.08 | w | br |
| 50.02 | 1.82 | m | |

EXAMPLES 7-9

UZM-27 compositions are crystalline microporous zeolites derived from the calcination of the as-synthesized UZM-27P precursors. Examples 7-9 present the synthesis of UZM-27 from UZM-27P at various conditions. The results from these examples are presented in Table 4 along with surface area analysis results. The calcination was carried out under a flow of either nitrogen or dry air, ramping first at 1° C./min to 350° C., holding for an hour, ramping at 1° C./min to the calcination temperature indicated in Table 4 and holding at that temperature for the amount of time indicated. Once at the calcination temperature, dry air was employed for the remainder of the calcination. After calcination, the materials were to characterized by XRD analysis. The representative diffraction lines for each UZM-27 composition are shown in Tables 5-10. The BET method was used to obtain the surface area data.

TABLE 4

| Example | Parent UZM-27P | Calcination Conditions | Surface Area; Micropore Volume (BET) | Diffraction Table |
|---|---|---|---|---|
| 7 | Example 4 | 525° C., dry air, 6 hr | 184 m²/g; 0.035 cc/g | Table 5 |
| 8 | Example 5 | 540° C., N2, dry air, 4 hr | 207 m²/g; 0.065 cc/g | Table 5 |
| 9 | Example 6 | 525°, dry air, 6 hr | 252 m²/g; 0.083 cc/g | Table 6 |

TABLE 5

| Example 7 | | | | Example 8 | | | |
|---|---|---|---|---|---|---|---|
| 2Θ | d(Å) | I/I₀ % | peaks | 2Θ | d(Å) | I/I₀ % | peaks |
| 4.16 | 21.24 | vs | | 4.47 | 19.75 | m | |
| 8.25 | 10.70 | m | | 10.04 | 8.8 | m | |
| 9.55 | 9.26 | m | | 10.65 | 8.3 | m | |
| 10.42 | 8.48 | m | | 13.3 | 6.65 | s | |
| 12.82 | 6.90 | s | | 19.78 | 4.48 | m | br |
| 19.74 | 4.49 | m | br | 21.42 | 4.15 | m | br |
| 21.62 | 4.11 | m | br | 24.66 | 3.61 | s | sh |
| 24.36 | 3.65 | m | sh | 26.26 | 3.39 | vs | br |
| 25.8.0 | 3.45 | vs | br | 29.92 | 2.98 | m | br |
| 30.06 | 2.97 | m | br | 50.04 | 1.82 | m | |
| 50.00 | 1.82 | m | | | | | |

TABLE 6

| Example 9 | | | |
|---|---|---|---|
| 2Θ | d(Å) | I/I₀ % | peaks |
| 4.14 | 21.33 | m | |
| 9.78 | 9.03 | m | |
| 10.63 | 8.32 | m | |
| 13.00 | 6.80 | vs | |
| 19.64 | 4.52 | s | br |
| 21.44 | 4.14 | m | br |
| 24.62 | 3.61 | s | sh |
| 26.34 | 3.38 | vs | br |
| 30.86 | 2.89 | m | br |
| 49.82 | 1.83 | m | |

The invention claimed is:

1. A hydrocarbon conversion process selected from the group consisting of alkylation, isomerization, olefin dimerization and oligomerization, and dewaxing comprising contacting a hydrocarbon stream with a crystalline microporous zeolitic composition at hydrocarbon conversion conditions to give a converted product, the crystalline zeolitic microporous composition having a three-dimensional framework composed of at least tetrahedral $SiO_2$ units and an empirical composition on an anhydrous basis expressed by the empirical formula of:

$$M_m^{n+}Al_{1-x}E_xSi_yO_z$$

where M is at least one exchangeable cation selected from the group consisting of hydrogen ion, alkali, alkaline earth, and rare earth metals, "m" is the mole ratio of M to (Al+E) and varies from 0.05 to about 10.0, "n" is the weighted average valence of M and has a value of about 1 to about 3, E is an element selected from the group consisting of gallium, iron, boron and mixtures thereof, "x" is the mole fraction of E and has a value from 0 to about 1.0, "y" is the mole ratio of Si to (Al+E) and varies from greater than 10 to about 35 and "z" is the mole ratio of O to (Al+E) and has a value determined by the equation:

$$z=(m \cdot n+3+4 \cdot y)/2$$

and is characterized in that it has the x-ray diffraction pattern having at least the d-spacings and intensities set forth in Table B:

TABLE B

| 2Θ | d(Å) | I/I₀ % | peaks |
|---|---|---|---|
| 4.03-4.57 | 21.91-19.32 | m-vs | |
| 9.40-10.20 | 9.40-8.67 | m | |
| 10.25-10.80 | 8.62-8.19 | m | |
| 12.65-13.45 | 6.99-6.58 | s-vs | |
| 19.55-19.87 | 4.54-4.46 | m-s | br |
| 21.32-21.72 | 4.16-4.09 | m | br |
| 24.25-24.75 | 3.67-3.59 | m-s | sh |
| 25.65-26.48 | 3.47-3.36 | vs | br |
| 29.75-31.01 | 3.00-2.88 | m | br |
| 49.72-50.13 | 1.83-1.82 | m. | |

2. The process of claim 1 where M is selected from the group consisting of Li, Na, K, Cs, Ca, Ba, Sr, La and Yb.

* * * * *